(12) United States Patent
Nelson et al.

(10) Patent No.: US 6,950,495 B2
(45) Date of Patent: Sep. 27, 2005

(54) BACKSCATTER IMAGING USING HADAMARD TRANSFORM MASKING

(75) Inventors: James M. Nelson, Sumner, WA (US); William B. Shepherd, Vashon, WA (US)

(73) Assignee: The Boeing Company, Chicago, IL (US)

(*) Notice: Subject to any disclaimer, the term of this patent is extended or adjusted under 35 U.S.C. 154(b) by 55 days.

(21) Appl. No.: 10/725,836

(22) Filed: Dec. 1, 2003

(65) Prior Publication Data

US 2005/0117701 A1 Jun. 2, 2005

(51) Int. Cl.$^7$ .......................... G01N 23/20; G21K 3/00
(52) U.S. Cl. ........................ 378/87; 378/156; 378/2; 382/281; 382/283
(58) Field of Search .................. 378/87, 156, 2; 382/281, 283

(56) References Cited

U.S. PATENT DOCUMENTS

| | | | |
|---|---|---|---|
| 3,748,470 A | 7/1973 | Barrett | |
| 3,775,602 A | 11/1973 | Alexandridis et al. | |
| 3,936,639 A * | 2/1976 | Barrett | ........................... 378/2 |
| 3,969,699 A | 7/1976 | McGlaughlin | |
| 3,982,227 A | 9/1976 | Joynson et al. | |
| 4,005,385 A | 1/1977 | Joynson et al. | |
| 4,075,483 A * | 2/1978 | Tancrell et al. | ................. 378/2 |
| 4,241,404 A * | 12/1980 | Lux | ............... 378/2 |
| 4,549,212 A | 10/1985 | Bayer | |
| 4,621,337 A | 11/1986 | Cates et al. | |
| 4,809,312 A | 2/1989 | Annis | |
| 4,819,256 A | 4/1989 | Annis et al. | |
| 4,974,247 A | 11/1990 | Friddell | |
| 5,033,073 A | 7/1991 | Friddell | |
| 5,157,743 A | 10/1992 | Maeda et al. | |
| 5,181,234 A | 1/1993 | Smith | |
| 5,247,354 A | 9/1993 | Nakajima | |
| 5,293,434 A | 3/1994 | Feig et al. | |
| 5,606,165 A * | 2/1997 | Chiou et al. | ........... 250/363.06 |
| 5,926,488 A | 7/1999 | Khayrallah | |
| 6,094,472 A | 7/2000 | Smith | |
| 6,205,195 B1 * | 3/2001 | Lanza | ........................ 376/157 |
| 6,370,222 B1 | 4/2002 | Cornick, Jr. | |
| 6,473,487 B1 | 10/2002 | Le | |
| 6,487,236 B1 | 11/2002 | Iwamatsu et al. | |
| 2002/0028021 A1 | 3/2002 | Foote et al. | |
| 2002/0080760 A1 | 6/2002 | Anja et al. | |
| 2003/0202634 A1 * | 10/2003 | Gerchberg | .................. 378/147 |
| 2004/0095626 A1 * | 5/2004 | Brady | ........................ 359/237 |

FOREIGN PATENT DOCUMENTS

| | | |
|---|---|---|
| EP | 0920185 | 6/1999 |
| EP | 1012986 | 6/2000 |

(Continued)

OTHER PUBLICATIONS

U.S. Appl. No. 07/124,616, filed Nov. 24, 1987, Application was abandoned.

(Continued)

*Primary Examiner*—Craig E. Church
*Assistant Examiner*—Krystyna Sucheski
(74) *Attorney, Agent, or Firm*—Thompson Coburn LLP

(57) ABSTRACT

Backscatter imaging using Hadamard transform masking includes an area x-ray source with alternating, masked, Hadamard transform patterns. The total backscatter signal from a target for each pair of corresponding masks is recorded. The difference in signal strengths for each pair of corresponding masks is a direct measurement of the Hadamard transform coefficient for that mask. An image of the target is formed by performing an inverse discrete Hadamard transform on the complete matrix of coefficients.

18 Claims, 2 Drawing Sheets

FOREIGN PATENT DOCUMENTS

| EP | 1024456 | 8/2000 |
|---|---|---|
| EP | 1173027 | 1/2002 |
| WO | WO 8500906 | 2/1985 |
| WO | WO 8500908 | 2/1985 |
| WO | WO 9202937 | 2/1992 |
| WO | WO 9909655 | 2/1999 |
| WO | WO 00/01157 | 6/1999 |
| WO | WO 00/49428 | 8/2000 |

OTHER PUBLICATIONS

Decker, J.A.: Hadamard-Transform Image Scanning; Applied Optics, vol. 9 No. 6, Jun. 1970, 4 pages.

Appendix B, X-Ray-Based Detection Systems; Technology Against Terrorism: The Federal Effort;Internet article: 4 pages, May 13, 2003: http://216.239.37.104/searc.../913909.pdf.

AS&E Announces Breakthrough in X-Ray Inspection Technology; Press Release; Internet Article; 2 pages, www.as-e.com/about/2001/070901.html; May 13, 2003.

AS&E Technology; Internet article; May 13, 2003; 2 pages, www.as-e.com/technogy/backscatter.html.

Bossi, RH, Friddell, K.D., Nelson, J.M.; Backscatter X-Ray Imaging; Materials Evaluation; Vol. 46, No. 11, Oct. 1989: 10 pages.

* cited by examiner

BACKSCATTER IMAGING USING HADAMARD TRANSFORM MASKING

BACKGROUND OF THE INVENTION

The present invention is directed to backscatter imaging, and more specifically such imaging utilizing Hadamard transform masking.

One x-ray imaging approach has been Compton backscatter imaging using a flying spot x-ray source and a large x-ray detector on the same side of the target as the source. The collimation methods employed in these systems for scanning the x-ray beam over the target preclude the development of a portable, operationally convenient x-ray camera for on-site examination of large structures. This is primarily due to the competing requirements for a high x-ray fluence exposing the target at each scan position to improve signal to noise ratio for a fixed detector integration time, and the smallest possible diameter x-ray beam to improve the imaging resolution. For mechanical collimation schemes, these conflicting requirements result in high electrical power requirements for x-ray generation and extensive radiation shielding requirements degrading both portability and self-containment.

The present invention overcomes fundamental limitations of x-ray backscatter image formation associated with conventional flying spot spatial modulation of the x-ray beam. In accordance with the present invention, a nonscanning x-ray source is used, which increases incident x-ray fluence at the target by up to five orders of magnitude without requiring intensity modulation of the x-ray source and without any apparent additional thermal management or information degradation. The present invention fulfills the need for a fast, portable, one-sided x-ray backscatter imaging system and method.

SUMMARY OF THE INVENTION

Generally, in accordance with the present invention the target is illuminated with an area x-ray source with alternating, masked, Hadamard transform patterns, and the total backscatter signal for each pair of corresponding masks is recorded. The difference in signal strength for each pair of corresponding masks is a direct measurement of the Hadamard transform coefficient for that mask, in contrast to an individual image pixel value. The image is formed by performing an inverse Hadamard transform.

Further features and advantages of the present invention, as well as the structure and operation of various embodiments of the present invention, are described in detail below with reference to the accompanying drawings.

DETAILED DESCRIPTION OF THE PREFERRED EMBODIMENTS

The invention comprises a Hadamard transform masking method for sequentially illuminating a backscatter target with a series of spatially modulated complete, binary valued (on or off) x-ray patterns, or other radiation source patterns, in such a way that the image of the object can be reconstructed from the backscatter signal response at a single large area detector. While the invention has particular application for backscatter x-ray imaging, it is to be understood that it has other applications as well, including, for example, for optical, IR, acoustic, and other one-sided backscatter imaging applications.

In accordance with a preferred embodiment of the invention, a source of uniform illumination is provided to some form of modulation device that masks it to produce Walsh function illumination at the surface of a large area photocathode. The intensity of the light and its color must be such as to produce photoelectron currents at each pixel sufficient to produce a required X-ray flux. The light falling on the photocathode produces electrons in a vacuum space between two parallel electrodes, cathode and anode. An acceleration voltage numerically equal to the desired X-ray energy is imposed between the cathode and anode. When the electrons strike the anode, X-rays are generated with the flux peaked in the direction of the electron velocity. This X-ray flux is projected through a pinhole towards the target to be examined. Additional conducting grids may be located between the cathode and anode to provide proper control of the generation process. Also, a honeycomb-like electron collimation structure may be provided in the vicinity of the cathode to help isolate pixels from one another.

Figure 1:
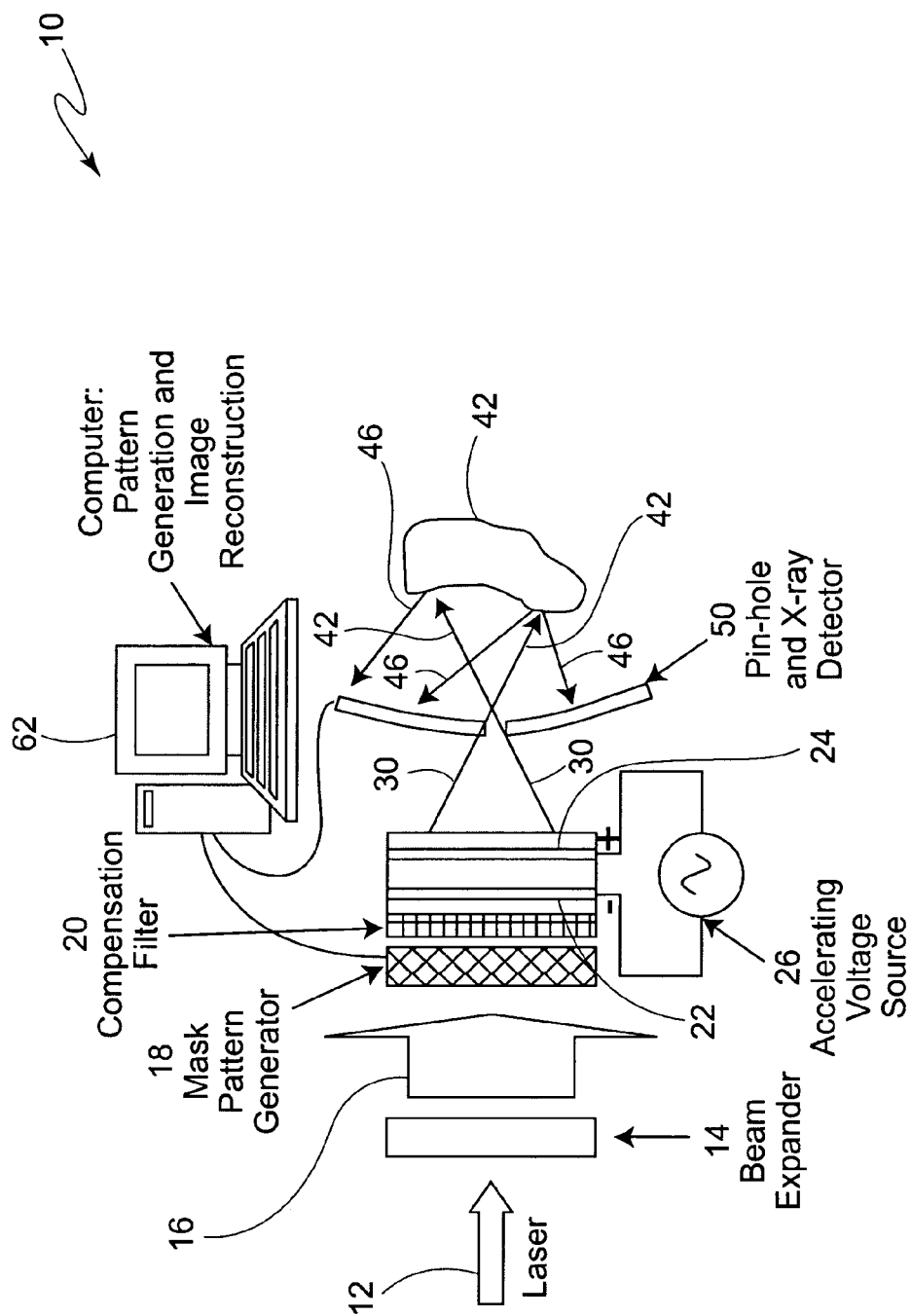
FIG. 1 is a schematic illustrating the structure and method of a preferred embodiment of the invention.

More specifically, with reference to FIG. 1 of the drawing, there is shown an x-ray camera configuration 10 for backscatter imaging using Hadamard transform masking in accordance with a preferred embodiment of the invention. A collimated laser source 12 is directed toward a laser beam expander 14 to produce an expanded laser beam 16. The beam 16 is directed toward an addressable, spatial modulator, matrix mask pattern generator 18. The mask generator 18 may be a square array of liquid crystal opaquing elements. In accordance with another embodiment of the invention, the collimated laser beam and liquid crystal array may be replaced by a square matrix of integrated diode lasers, in which case the laser diodes may be modulated "on" and "off" to generate the Walsh functions, thus eliminating the liquid crystal array. With either embodiment, spatially modulated light is directed through a compensation filter 20 to a photo-cathode 22 where it is absorbed to produce a spatially modulated electron flux. The electrons are then accelerated to an anode 24 by accelerating voltage source 26. Electrons striking the anode 24 produce a similarly spatially modulated x-ray source pattern in accordance with the particular mask at the mask generator 18. X-ray emissions 30 from the anode 24 are beamed through a pinhole 32 and onto an object (target) 40 being tested to illuminate the object with multiple x-ray beamlets 42. Impingement of the beamlets 42 onto the object 40 creates reflected backscatter x-ray beams 46 which are detected by a large area detector 50.

A suitable computer 60, well-known in the art, generates signals input to the mask pattern generator 18 to generate the masks in accordance with the invention. Computer 60 also processes the detected x-ray backscatter characteristics 46 of the object 50 by recording the total backscatter signal for each pair of corresponding masks, computing the difference in signal strengths for such pair of corresponding masks, and performing an inverse Hadamard transform to form an x-ray image of the target on a display 62.

The Hadamard transform is a computationally efficient method for image coding. This computational efficiency is realized by the binary valued nature of the Walsh functions (designated CAL and SAL) which evaluate to either one (1) or minus one (−1), depending on the value of x. This means that all of the Walsh functions up to order n can be represented by n×n bits, and evaluated by a bit table look up.

Using the Hadamard transform, an "image" (function of two variables) can be expressed as n×n Hadamard transform matrix of floating coefficients (function of sequency) by convolving the image with each of the n×n two dimensional Walsh functions up to sequency (n,n). The convolving functions in the Hadamard transform are only binary valued (1 or −1) such that each Hadamard transform coefficient for an image can be measured directly by illuminating the image with a series of masks and reading the output of a large area light detector.

In accordance with a preferred embodiment of the invention, to apply the Hadamard transform masking method to x-ray backscatter imaging, either a collimated laser light beam is projected through a square array of liquid crystal opaquing elements, or a square (n×n) matrix of integrated diode lasers is used to provide spatially modulated illumination of a photo-cathode, energized and evacuated in a configuration suitable for the production of x-rays at a suitable anode. In each such case, positive and negative mask patterns are alternately generated, corresponding to each of the two dimensional Walsh functions up to the sequency corresponding to the smallest liquid crystal mask, or laser diode element, as the case may be, (W(n,n)). With the use of the photo-cathode and anode pair, a small pinhole in the center of an x-ray opaque material is placed at a suitable location in front of the anode between the photo-cathode and the target. This results in exposure of the entire solid angle of the target aperture with (2×n×n) different patterns of spatially modulated x-ray beams.

Figure 2B:
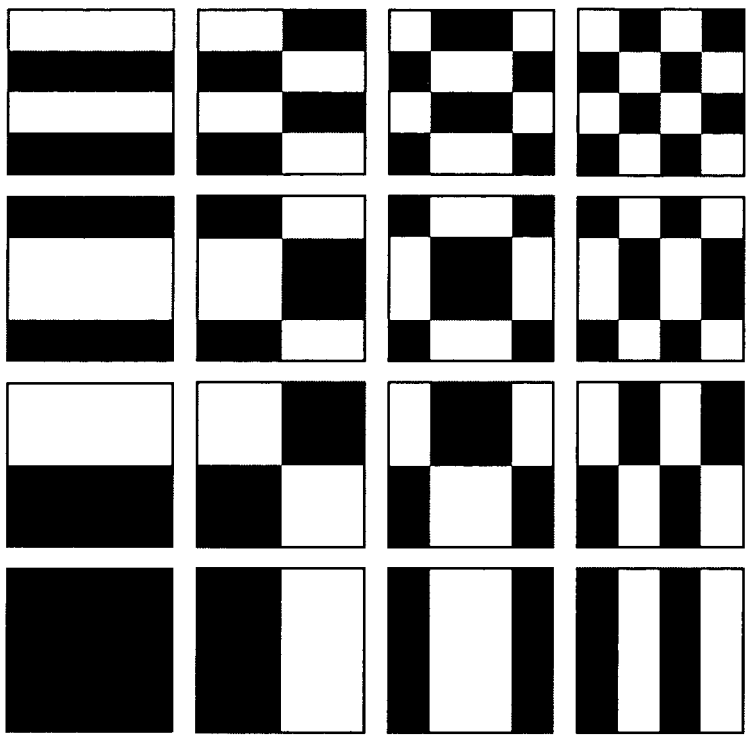
FIG. 2 shows samples of masks used to illustrate a preferred embodiment of the invention.
Figure 2A:
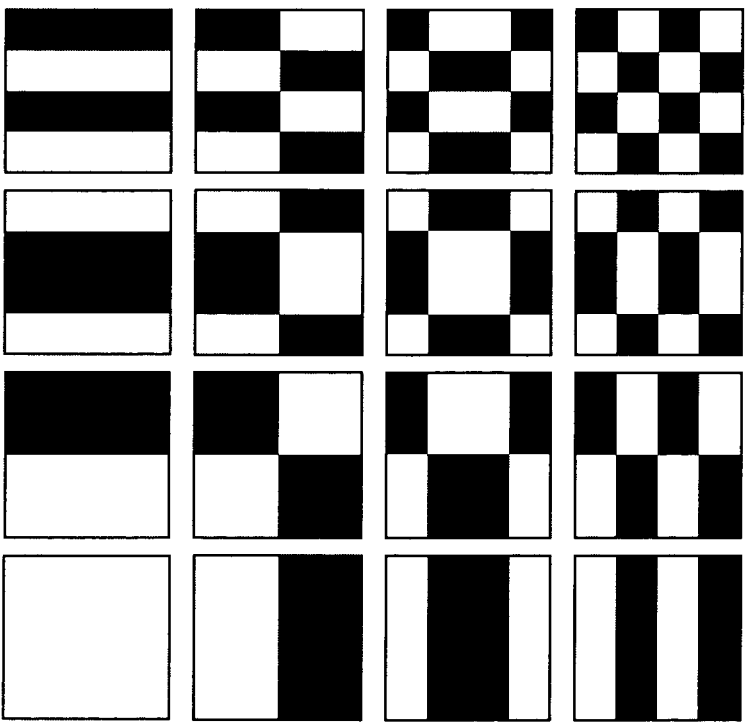

The difference between the two responses at the detector:

(a) the target illuminated with the positive Walsh pattern, and (b) the target illuminated by the corresponding negative Walsh pattern is a single numerical value representing the projection of the target image on the corresponding Hadamard transform basis function. For example, FIG. 2 shows a set of 32 Hadamard transform masks (16 pairs of positive and negative masks) for an image of 4×4 pixels. The differencing of the result of two masks in each pair is done because the Walsh function basis takes on values of +1 and −1 but only positive illumination (+1) is possible to implement in a physical device. The unique properties of orthogonal basis functions, including Walsh functions, unlike other non-orthogonal functions such as simple square waves, is that the image can be recomposed by multiplying each basis function by each numerical value from its projection on the image function to reconstitute the image. This post-process multiplication of the complete set of values ("discrete Hadamard transform coefficients") by the corresponding Walsh functions is described mathematically as "performing the inverse discrete Hadamard transform". The discrete Hadamard transform for the Hadamard masking in accordance with this invention may be expressed as follows:

$$F(u, v) = \frac{1}{\sqrt{MN}} \sum_{u=0}^{M-1} \sum_{v=0}^{N-1} [f(x, y)\text{sgn}(W_{xy}(u, v)) - f(x, y)\text{sgn}(-W_{xy}(u, v))]$$

where the term $f(x,y)\text{sgn}(W_{xy}(u,v))$ is measured by the positive mask exposure, and the term $f(x,y)\text{sgn}(-W_{xy}(u,v))$ is measured by the negative mask exposure.

The difference between the integrated backscatter signal from the positive and negative masks corresponding to the (i,j)th Walsh function (W(ij)) becomes the Hadamard transform coefficient for that Walsh function. The image is calculated as the sum of the n×n coefficients times the corresponding two dimensional Walsh function (which only takes on the values 1 or −1).

Only the initial signal differencing and the last summing step require any floating point processing, as both the generation of and multiplication by Walsh functions are simple gate array parallel logic steps. Walsh functions are preferred, because, other than the Kroneker delta function (which is effectively the mask defined by a conventional flying spot source), only Walsh functions (1) are both binary valued (eliminating the requirement for x-ray intensity modulation) and (2) form a set of orthogonal basis functions spanning the space of all n×n two dimensional images. No binary valued orthogonal basis sets other than Walsh functions and the Kroneker delta function are known to exist.

Time dependent x-ray intensity variations are handled by normalizing detector output to electron current in the x-ray generator. In order for the X-ray detector current from each pattern to be used, it is necessary to know the total X-ray flux projected towards the target. This is proportional to the generating current and must be the same from one pattern to the next. Since that is generally not achievable to required precision, it is desirable to measure the total current flowing into the photocathode and adjust each X-ray detector current in proportion to normalize the x-ray detector output.

Pixel-to-pixel variations in electron generation efficiency as a result of local variations in geometry and photocathode response to the incident laser flux may be addressed by engineering the illumination system and photocathode to minimize this problem. If the variations are reproducible over time, a compensation filter may be incorporated with the photocathode to adjust the illumination distribution to obtain equal X-ray generation from each pixel of the anode. If, instead of a collimated beam from a single laser, an array of solid state laser diodes is used, each one being assigned to an individual pixel of the cathode, the X-ray generation efficiency may be balanced by tuning each of the diode outputs, thus eliminating the compensation filter.

Alternatively, the illumination source may be a light panel such as is used in computer flat panel displays. As a further alternative, light emitting diodes in an array may be used rather than laser diodes.

The x-ray backscatter imaging using the Hadamard transform masking method of this invention has the practical advantage that beam scanning is not required, although it is somewhat more computationally complex than with the use of single spot scanning. Since, on average, each Hadamard transform mask is half on and half off, the deliverable x-ray flux through an equivalent pinhole is 0.5×n×n higher than for a single spot "mask". For a typical 512×512 pixel image, this translates to five orders of magnitude increase in flux for each signal integration interval. This feature of the invention offers a solution to the fundamental fluence limit problem associated with earlier approaches with only a modest increase in computational complexity.

Thus, there has been described backscatter imaging utilizing Hadamard transform masking that fulfills the need for a fast, portable, one-sided x-ray backscatter imaging system and method which significantly increases incident x-ray fluence at the target without requiring intensity modulation of the x-ray source and without additional thermal management or information degradation.

While the present invention has been described by reference to specific embodiments and specific uses, it should be understood that other configurations and arrangements could be constructed, and different uses could be made, without departing from the scope of the invention as set forth in the following claims.

What is claimed is:

1. A method of x-ray imaging, said method comprising the steps of:
    illuminating a target with an area x-ray source using Hadamard transform mask patterns, creating reflected backscatter x-ray signals;
    detecting said backscatter x-ray signals; and
    conducting an inverse Hadamard transform utilizing said backscatter signals to form an image of said target.

2. A method of x-ray imaging, said method comprising the steps of:
    illuminating a target with an area x-ray source using pairs of Hadamard transform patterns, each pair comprising alternating mask patterns;
    recording the total backscatter signal for each mask of each pair of masks;
    performing an inverse Hadamard transform using the difference in backscatter signal strengths of the alternating masks in each pair of masks; and
    forming an image of the target from said inverse Hadamard transform.

3. A method of x-ray imaging, said method comprising the steps of:
    directing a collimated laser beam, after having been acted upon by an addressable, spatial modulator, matrix mask, to a photo-cathode to generate a spatially modulated electron flux at the surface of the photocathode;
    accelerating said electron flux from said photo-cathode to an anode, producing at said anode an x-ray source pattern in accordance with the mask pattern at said spatial modulator mask;
    beaming x-ray emissions from said anode through a pinhole onto a target to illuminate said target with multiple x-ray beamlets, said beamlets impinging on said target creating reflected backscatter x-ray signals;
    detecting said backscatter x-ray signals;
    modulating said spatial modulator matrix mask using pairs of transform patterns, each pair comprising alternating mask patterns;
    recording the total backscatter signal for each mask of each pair of masks;
    performing an inverse Hadamard transform using the difference in backscatter signal strengths of the alternating masks in each pair of masks; and
    forming an image of the target from said inverse Hadamard transform.

4. A method of x-ray imaging, said method comprising the steps of:
    directing a collimated laser beam toward an addressable, spatial modulator, matrix mask;
    producing an x-ray source pattern in accordance with the mask pattern at said spatial modulator mask;
    beaming x-ray emissions from said x-ray source pattern to illuminate a target with multiple x-ray beamlets, said beamlets impinging upon said target creating reflected backscatter x-ray signals;
    detecting said backscatter x-ray signals;
    modulating said spatial modulator matrix mask using pairs of Hadamard transform patterns, each pair comprising alternating mask patterns;
    performing an inverse Hadamard transform from said backscatter signals; and
    forming an image of the target utilizing said inverse Hadamard transform.

5. The method of claim 4 further comprising the steps of:
    recording the total backscatter signal for each mask of each pair of masks;
    performing an inverse Hadamard transform using the difference in backscatter signal strengths of the alternating masks in each pair of masks; and
    forming an image of the target from said inverse Hadamard transform.

6. An apparatus for x-ray imaging, said apparatus comprising:
    an area x-ray source for illuminating a target with x-ray patterns defined by Hadamard transform mask patterns, thereby creating reflected backscatter x-ray signals from said target;
    a detector for detecting said backscatter x-ray signals; and
    a display for displaying an image of said target, said image formed from an inverse Hadamard transform utilizing said backscatter signals.

7. The apparatus of claim 6 wherein said x-ray source illuminates the target using pairs of Hadamard transform patterns, each pair comprising alternating mask patterns, said apparatus further comprising a recorder for recording the total backscatter signal for each mask of each pair of masks, and wherein said image of the target is formed from an inverse Hadamard transform using the difference in backscatter signal strengths of the alternating masks in each pair of masks.

8. An apparatus for x-ray imaging, said apparatus comprising:
    a source of collimated laser beams;
    an addressable, spatial modulator, matrix mask, said laser beam source directing said collimated laser beams toward said matrix mask;
    x-ray source patterns producing x-ray emissions in accordance with mask patterns at said matrix mask to illuminate a target with multiple x-ray beamlets, the impingement of said beamlets upon said target creating reflected backscatter x-ray signals;
    a detector for detecting said backscatter x-ray signals;
    a modulator for modulating said matrix mask using pairs of Hadamard transform patterns, each pair comprising alternating mask patterns; and
    a display for displaying an image of said target, said image created by performing an inverse Hadamard transform from said backscatter signals.

9. The apparatus of claim 8 further comprising:
    a recorder for recording the total backscatter signal for each mask of each pair of masks;
    said image of said target being formed by performing an inverse Hadamard transform using the difference in backscatter signal strengths of the alternating masks in each pair of masks.

10. An apparatus for x-ray imaging, said apparatus comprising:
    a collimated laser beam source;
    an addressable, spatial modulator, matrix mask, said laser beam source directing collimated laser beams toward said matrix mask;
    a photo-cathode receiving laser beams from said matrix mask;
    an anode for receiving accelerated electrons from said photo-cathode and for transmitting x-ray beams to a target thereby illuminating said target and creating reflected backscatter x-ray signals from said target;

a detector for detecting said backscatter x-ray signals;

a modulator for modulating said matrix mask using pairs of transform patterns, each pair comprising alternating mask patterns;

a recorder for recording the total backscatter signal for each mask of each pair of masks; and a display for displaying an image of said target, said image formed by performing an inverse Hadamard transform using the difference in backscatter signal strengths of the alternating masks in each pair of masks.

11. A method of imaging, said method comprising the steps of:

illuminating a target with an area illumination source using Hadamard transform mask patterns, creating reflected x-ray backscatter signals;

detecting said x-ray backscatter signals; and conducting an inverse Hadamard transform utilizing said backscatter signals to form an image of said target.

12. A method of imaging, said method comprising the steps of:

illuminating a target with an area illumination source using pairs of Hadamard transform patterns, each pair comprising alternating mask patterns, to produce x-ray backscatter signals from said target;

recording the total x-ray backscatter signal for each mask of each pair of masks;

performing an inverse Hadamard transform using the difference in backscatter signal strengths of the alternating masks in each pair of masks; and forming an image of the target from said inverse Hadamard transform.

13. A method of x-ray imaging, said method comprising the steps of:

directing illumination rays toward an addressable, spatial modulator, matrix mask;

producing an x-ray source pattern in accordance with the mask pattern at said spatial modulator mask;

beaming emissions from said x-ray source pattern to illuminate a target creating reflected backscatter signals;

detecting said backscatter signals;

modulating said spatial modulator matrix mask using pairs of Hadamard transform patterns, each pair comprising alternating mask patterns;

performing an inverse Hadamard transform from said backscatter signals; and forming an image of the target utilizing said inverse Hadamard transform.

14. The method of claim 13 further comprising the steps of:

recording the total backscatter signal for each mask of each pair of masks;

performing an inverse Hadamard transform using the difference in backscatter signal strengths of the alternating masks in each pair of masks; and forming an image of the target from said inverse Hadamard transform.

15. An apparatus for imaging, said apparatus comprising:

an area illumination source for illuminating a target with beam emissions defined in accordance with Hadamard transform mask patterns, said beam emissions creating reflected x-ray backscatter signals from said target;

a detector for detecting the x-ray backscatter signals, and a display for displaying an image of said target, said image formed from an inverse Hadamard transform utilizing said backscatter signals.

16. The apparatus of claim 15 wherein said source illuminates the target using pairs of Hadamard transform patterns, each pair comprising alternating mask patterns, said apparatus further comprising a recorder for recording the total backscatter signal for each mask of each pair of masks, and wherein said image of the target is formed from an inverse Hadamard transform using the difference in backscatter signal strengths of the alternating masks in each pair of masks.

17. An apparatus for imaging, said apparatus comprising:

a source of beams;

an addressable, spatial modulator, matrix mask, said beam source directing said beams toward said matrix mask;

a source pattern produced in accordance with a mask pattern at said matrix mask, said source pattern generating emissions to illuminate a target thereby creating reflected x-ray backscatter signals;

a detector for detecting said x-ray backscatter signals;

a modulator for modulating said matrix mask using pairs of Hadamard transform patterns, each pair comprising alternating mask patterns; and a display for displaying an image of said target, said image created by performing an inverse Hadamard transform from said backscatter signals.

18. The apparatus of claim 17 further comprising:

a recorder for recording the total backscatter signal for each mask of each pair of masks;

said image of said target being formed by performing an inverse Hadamard transform using the difference in backscatter signal strengths of the alternating masks in each pair of masks.

* * * * *